(12) United States Patent
Lin

(10) Patent No.: US 7,147,648 B2
(45) Date of Patent: Dec. 12, 2006

(54) DEVICE FOR CUTTING AND HOLDING A CORNEA DURING A TRANSPLANT PROCEDURE

(75) Inventor: James Lin, Poulsbo, WA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 742 days.

(21) Appl. No.: 10/615,059

(22) Filed: Jul. 8, 2003

(65) Prior Publication Data

US 2005/0010243 A1    Jan. 13, 2005

(51) Int. Cl.
*A61B 17/32* (2006.01)

(52) U.S. Cl. ........................... 606/166; 623/4.1

(58) Field of Classification Search ............ 606/166, 606/167, 168, 169, 184; 30/44, 125, 130; 623/4.1, 5.11
See application file for complete search history.

(56) References Cited

U.S. PATENT DOCUMENTS

| 4,190,050 A | 2/1980 | Bailey | 128/305.1 |
| 4,718,420 A | 1/1988 | Lemp | 128/310 |
| 4,744,362 A | 5/1988 | Gründler | 128/305 |
| 4,865,033 A | 9/1989 | Krumeich et al. | 128/346 |
| 4,884,570 A * | 12/1989 | Krumeich et al. | 606/166 |
| 5,288,292 A * | 2/1994 | Giraud et al. | 606/166 |

* cited by examiner

*Primary Examiner*—Michael J. Hayes
*Assistant Examiner*—Victor X. Nguyen
(74) *Attorney, Agent, or Firm*—John H. Runnels; Bonnie J. Davis

(57) ABSTRACT

A device and surgical method for promoting suitable grafting between a healthy donor cornea button and a recipient's healthy corneal tissue. The device is a cornea transplanter comprising a cutting device, a support block having a removable base plate, and a vacuum device. The cornea transplanter is capable of retaining healthy donor corneal tissue as it is buttoned and placed onto the recipient's eye, with minimal physical manipulation of the donor corneal tissue. Once the cornea button is properly positioned, sutures may be symmetrically placed around the cornea button, using suture grooves that guide the suture needle to a particular depth and length of pass.

13 Claims, 6 Drawing Sheets

DEVICE FOR CUTTING AND HOLDING A CORNEA DURING A TRANSPLANT PROCEDURE

This invention pertains to a surgical instrument, more particularly a corneal trephine instrument and method for transplanting a cornea.

The cornea is a transparent tissue covering the anterior portion of the eye. It serves as the main refractive component of the eye. Uniform curvature, clarity, and consistency are qualities necessary for the cornea to focus light rays on the retina properly. When any of these qualities are impaired or lost, light rays maybe improperly focused, or even prevented from reaching the retina, resulting in blindness or diminished vision. A cornea transplant is sometimes the most effective means for restoring vision caused by a defective cornea.

Cornea transplantation involves replacing a defective cornea with a healthy donor cornea. In a typical cornea transplant, the first step is to remove healthy corneal tissue from a deceased donor. Once the donor corneal tissue is removed, it is placed on a cutting block with the endothelial side (the "underside" or concave portion) of the cornea facing upwards. A circular portion of the donor corneal tissue, called a "cornea button," is then excised from the donor corneal tissue using a circular blade with a predetermined diameter, also referred to as a "corneal punch," by centering the corneal punch over the donor corneal tissue and pushing the corneal punch through the entire thickness of the cornea. Once the donor corneal tissue is buttoned, the peripheral remnants are removed, and the cornea button is moistened and covered. The defective cornea is then removed from the recipient's eye using a hand-held circular blade, called a "trephine," by centering the trephine over the diseased area and turning the trephine until the blade cuts most of the way into the defective cornea. The trephined tissue may then be removed using a pair of scissors or a straight blade. Once the defective tissue is removed, the cornea button is removed from the cutting block using a spatula, and is placed onto the recipient's eye. The cornea button is then sutured into position with the recipient's remaining corneal tissue.

A common cause for failure in many transplant surgeries is graft rejection. In a typical cornea transplant, a successful surgery will depend on proper maintenance of the endothelial tissue of the donor during the procedure. Manipulation or destruction of endothelial cells increases the likelihood of graft failure. Another important factor for a successful surgery is the accurate and symmetrical placement of sutures around the cornea button to maintain uniform curvature, consistency, and clarity.

U.S. Pat. No. 4,865,033 describes a device for holding a donor cornea, and obtaining lamellar slices of cornea of varying diameter by pressing the cornea against a bearing member using a clamping ring.

U.S. Pat. No. 4,744,362 describes an automated device for transplanting a cornea, comprising a three dimensional adjustable carrier, an axis adjustment instrument, a trephine and a transplanter for transplanting a cornea and holding the cornea until it heals. The transplanter comprises a holder, a shaft, and a suction pad having an inner suction zone for gripping the transplant cornea and an annular suction zone for gripping the trephination edge of the cornea to be joined to the transplant cornea.

U.S. Pat. No. 4,718,420 describes a device for reducing post-operative astigmatism in corneal transplant patients by centering a corneal-scleral button on a concave surface and applying suction to the concave surface to hold the button in position during trephining.

U.S. Pat. No. 4,190,050 describes a trephine instrument for removing and grafting corneal buttons, comprising a handle and a blade coaxially mounted on a cylindrical guide or stem. Suction is applied to the cornea during removal to prevent deformation of the corneal button.

An unfilled need exists for a surgical instrument that minimizes the need to physically manipulate donor corneal tissue during corneal transplantation, while retaining accurate and symmetrical placement.

I have discovered an inexpensive device and method for trephining and grafting between a healthy donor corneal tissue and a recipient's remaining corneal tissue. The novel cornea transplanting device retains the donor corneal tissue as it is buttoned and placed onto the recipient's eye. The device comprises a cutting device, a support block having a removable base plate, and a vacuum device. In one embodiment, a removable base plate comprises a proximal end having a concave surface with symmetrically distributed suction ports adapted to hold a cornea button against the surface, and a distal end having symmetrically distributed suture grooves adapted to pass equidistant sutures through the cornea button and surrounding tissue at nearly equal depth. Negative pressure supplied by the vacuum device is applied to the donor corneal tissue through suction ports adapted to hold the corneal tissue against the concave surface. Once a button is cut from the donor corneal tissue, the peripheral remnant can be removed without disturbing the cornea button. To facilitate placement of the cornea button, the removable base plate is dislodged from the support block and the cornea button is placed onto the eye with the endothelial side down, while maintaining a negative pressure on the cornea button. The cornea button is then sutured into position by passing sutures through the suture grooves. The sutures may be tied either before or after releasing the negative pressure.

The invention provides an inexpensive method for transplanting donor corneal tissue by using a device capable of holding corneal tissue, during buttoning and suturing, without physically manipulating the corneal tissue. The invention removes much of the artistry involved in corneal transplants, and makes the surgery more of a science by providing a template that guides the sutures and allows for adjustment of the sutures after transplantation. The basic design comprises a cutting device, a support block having a removable base plate with suction ports and suture grooves, and a vacuum device. The suture grooves should be adapted to complement the curvature of the suture needle, so that a suture needle can pass through both the cornea button and surrounding corneal tissue at an appropriate depth and length. The cutting blade is preferably made from a material capable of producing a razor sharp edge all the way around so as to cut a perfectly circular section from the donor corneal tissue, such as tungsten, or stainless steel. The remaining components may be made from a sturdy, resilient material such as steel or polytetrafluoroethylene. However, any other suitable material, such as various hard plastics, may also be employed.

There are several advantages to this device. The potential for damaging endothelial cells of the cornea tissue during transplantation is substantially reduced. There no longer exists a need to physically manipulate the cornea button, because it is held securely against the concave surface both during trephination and during subsequent transplantation. Second, post-operative astigmatism maybe substantially reduced. Sutures are symmetrically placed, either in an interrupted or a running fashion, around the cornea button at a nearly equal depth using a base plate with suture grooves that guide the suture needle to a particular depth and pass length. If the need should arise, modifications (e.g., suture adjustments or removal) may optionally be done post-operatively to further reduce the occurrence of post-operative astigmatism. Finally, epithelial defects may be substantially reduced due to the creation of a moisture chamber for the epithelium, and the minimization of the amount of manipulation of the cornea. The novel device allows for enhancement of the healing process and patient comfort following surgery by preservation of the epithelium.

Figure 1:
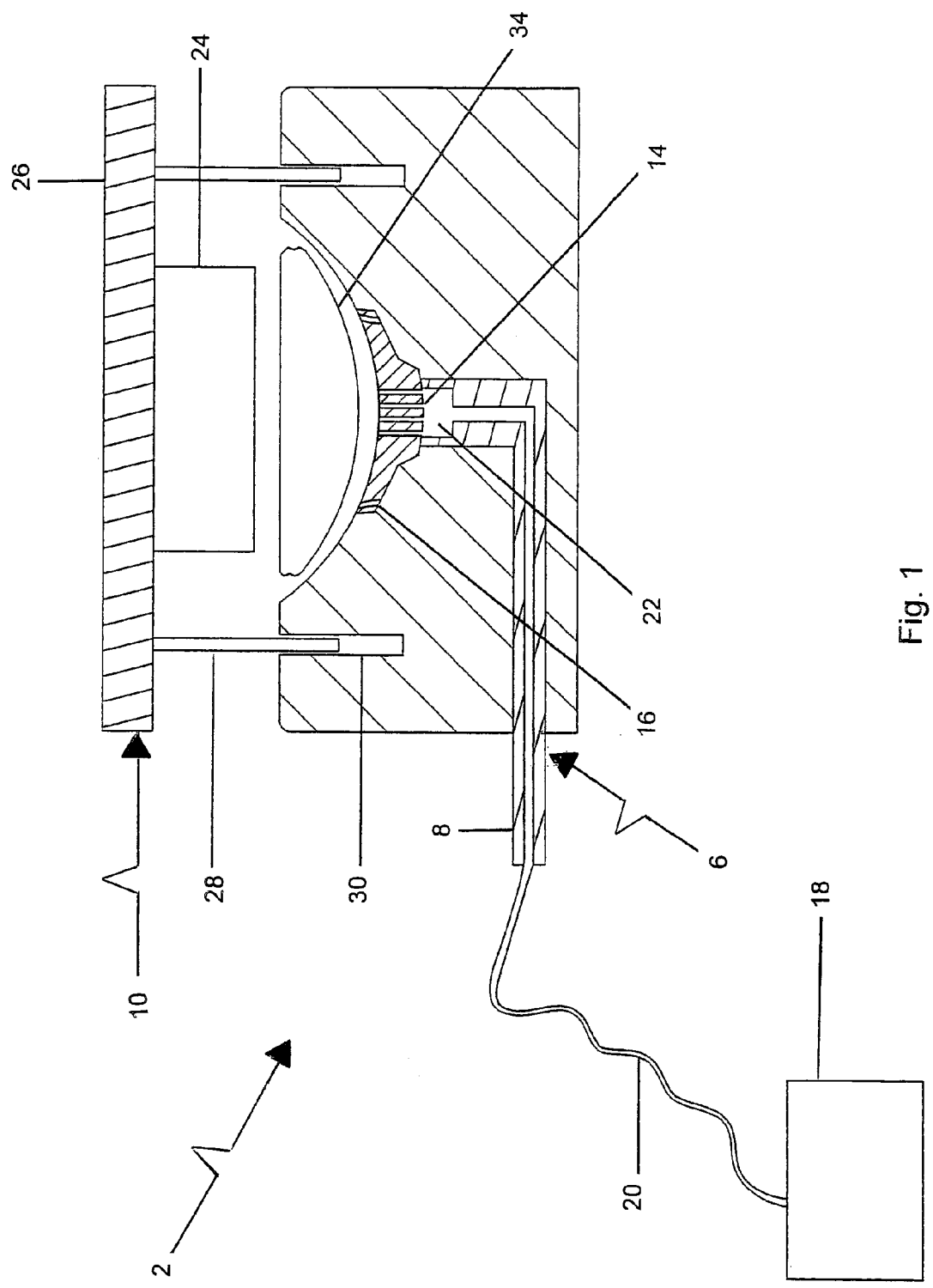
FIG. 1 illustrates a side sectional view of one embodiment of the novel trephine device.
Figure 2B:
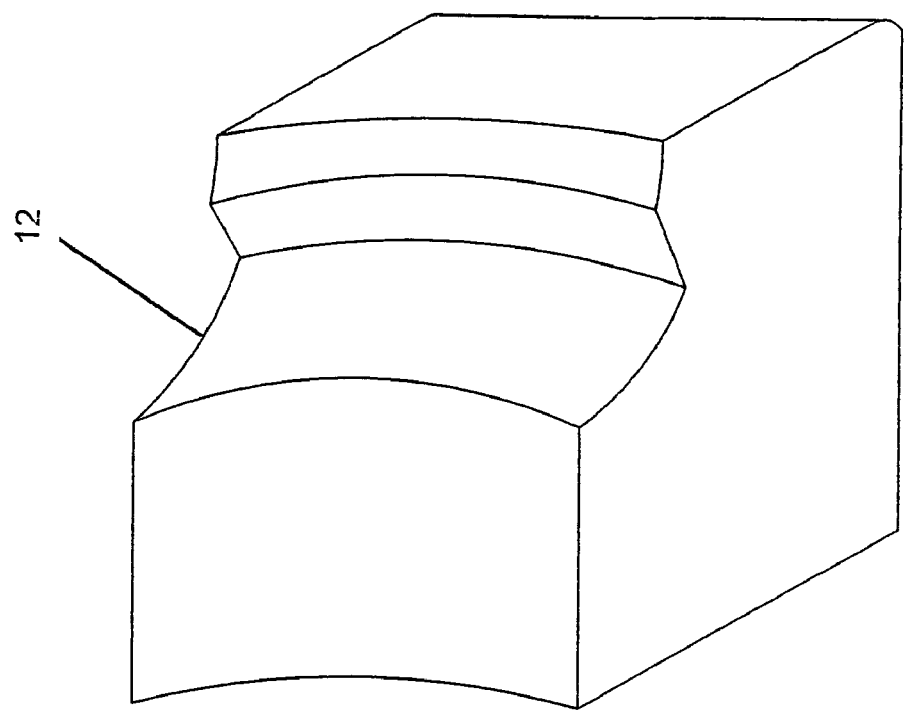
FIG. 2B illustrates a perspective view of one embodiment of the support block filler.
Figure 2A:
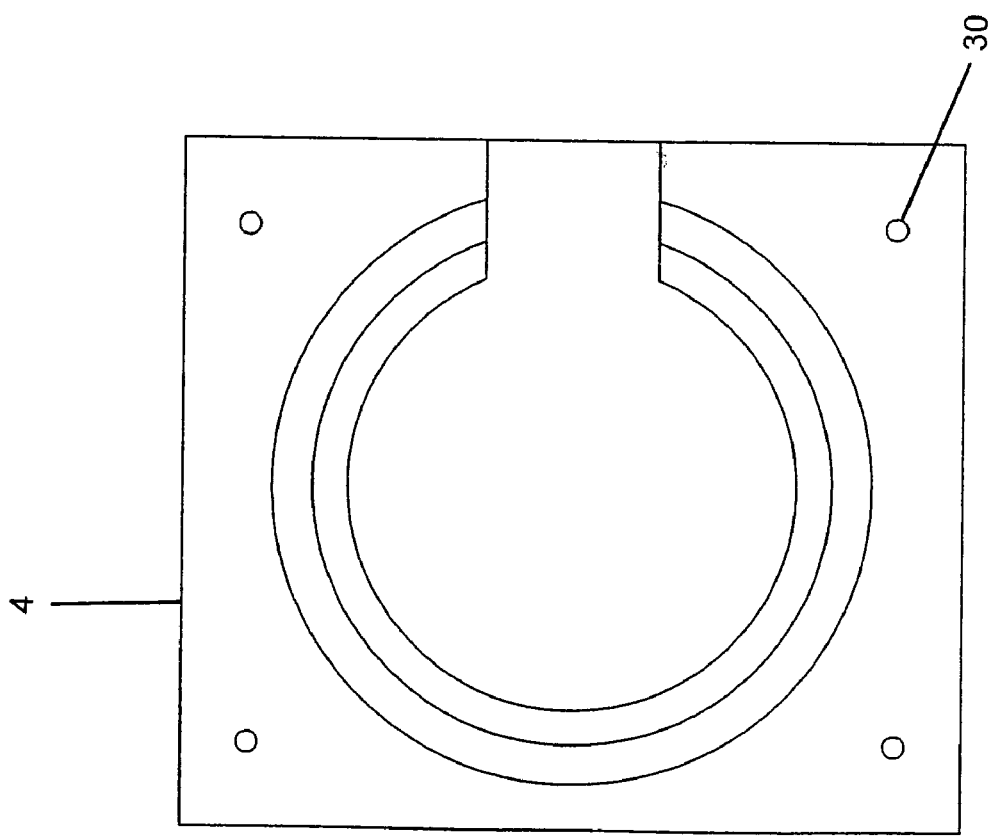
FIG. 2A illustrates a top plan view of one embodiment of the support block.

FIG. 1 illustrates one embodiment of a cornea transplanter 2, in accordance with the present invention. In this embodiment, cornea transplanter 2 comprises a support block 4, a removable base plate 6 having a handle 8, a cutting device 10, and a vacuum device 18. Support block 4 has a bore sized and shaped to receive removable base plate 6 and handle 8. See FIG. 2A. Once removable base plate 6 and support block 4 are combined, a support block filler 12 is inserted into the bore, so that removable base plate 6 and support block 4 form a smooth and continuous concave surface. See FIG. 2B. The curvature of the concave surface formed between removable base plate 6 and support block 4 is adapted to approximate that of the anterior surface of donor corneal tissue 34.

As illustrated in FIG. 1, removable base plate 6 is circular-shaped and comprises a proximal end having a concave surface with a plurality of suction ports 14 adapted to hold donor corneal tissue 34, and a distal end having a plurality of suture grooves 16 adapted to guide a suture needle through the cornea button and surrounding corneal tissue in the recipient's eye. In one embodiment, the size of removable base plate 6 is adapted to allow a portion of the outermost edge of the donor corneal tissue to extend beyond the outer edge of removable base plate 6 after the donor corneal tissue 34 has been buttoned and support block 4 removed. Preferably, removable base plate 6 is transparent, so that the cornea button and recipient's eye may be observed during transplantation.

As illustrated in FIG. 1, handle 8 is attached to removable base plate 6 to stabilize support block 4 during cornea buttoning, and to provide support for placing the cornea button on the recipient's eye. Negative pressure, which may be supplied through tubing 20 by vacuum device 18, enters through handle 8 into a hollow port 22 located at the bottom of removable base plate 6, and is distributed through suction ports 14 onto donor corneal tissue 34. Alternatively, handle 8 may be a syringe-type device (not shown) capable of maintaining a negative pressure on donor corneal tissue 34.

Figure 3:
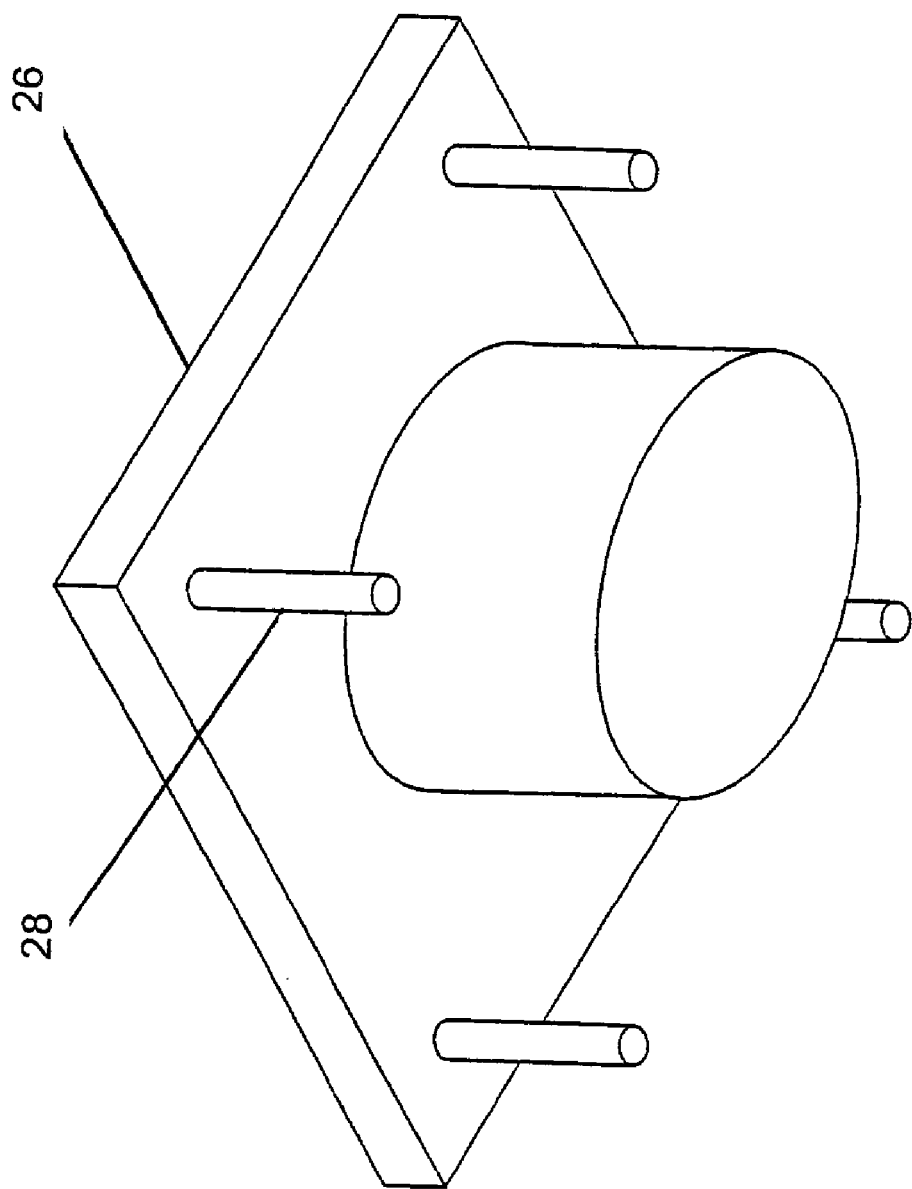
FIG. 3 illustrates a perspective view of one embodiment of the cutting device.

As illustrated in FIG. 1, cutting device 10 comprises a cutting blade 24 attached and centrally positioned on a lid 26. The dimensions and shape of cutting blade 24 are adapted to allow cutting blade 24 to cut a cornea button from donor corneal tissue 34 as lid 26 is pressed against support block 4. In an alternative embodiment, the diameter of cutting blade 24 is sized such that when donor corneal tissue 34 is cut, the outer edge of the cornea button extends slightly beyond the outer edge of removable base plate 6. In another embodiment, the diameter of cutting blade 24 is sized such that when the corneal tissue is cut, a portion of the outer edge of removable base plate 6 extends beyond that of the cornea button, which allows the surgeon to rest the outer edge on the recipient's remaining corneal tissue. Optionally, removable base plate 6 and support block 4 may be adapted to allow cutting blade 24 to pass into a groove (not shown) to ensure that the cornea button is completely cut. The diameter of the donor cornea button should be cut slightly larger than that of the corneal tissue removed from the recipient to inhibit post-operative flattening of the cornea. In a preferred embodiment, as lid 26 engages support block 4, inserts 28 positioned on the periphery of lid 26 engage with matching ports 30 located at each corner of support block 4. See FIGS. 2A and 3.

Figure 4:
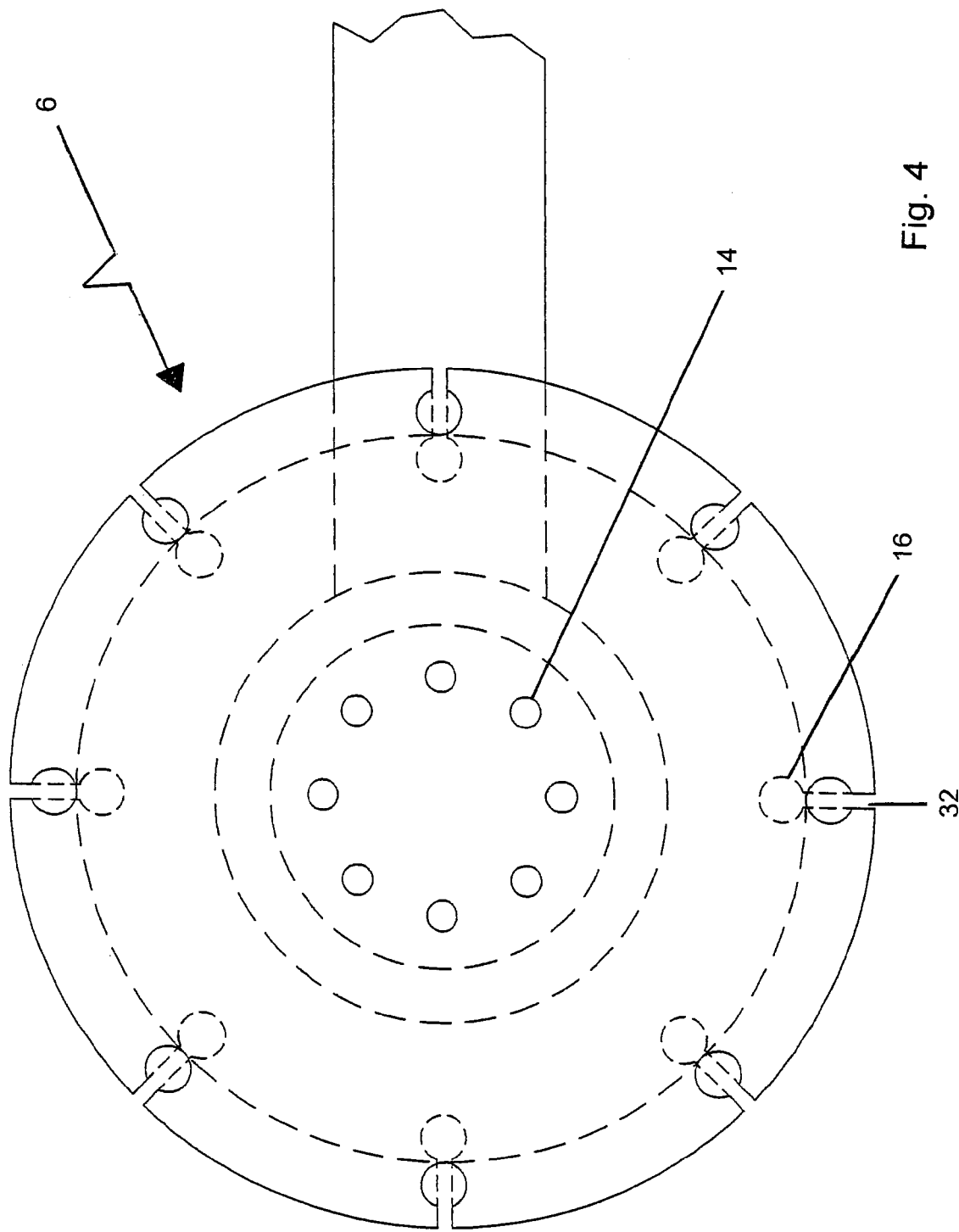
FIG. 4 illustrates a bottom plan view of one embodiment of the removable base plate.

FIG. 4 illustrates a bottom plan view of one embodiment of removable base plate 6. Corneal tissue is held securely against the concave surface of removable base plate 6 by applying negative pressure through suction ports 14. Suction ports 14 are centrally located and symmetrically distributed to support and stabilize donor corneal tissue during buttoning and subsequent transplantation of the cornea button. In this embodiment, eight suture grooves 16 are symmetrically distributed along the distal end of removable base plate 6 to guide the suture needle to a particular depth, and to maintain a certain length of suture passage. Alternatively, removable base plate 6 may comprise of suture grooves 16 (e.g., twelve or sixteen). Optionally, slits 32 are cut through each suture groove 16 to allow the suture to pass through the distal end of removable base plate 6 to prevent entanglement with removable base plate 6 as the needle exits the surrounding corneal tissue, and to allow for a running suture (i.e., one suture that connects all the suture grooves 16 together in a circular array) to pass through each suture groove 16. The dimensions and shape of the contact surface in suture grooves 16 complement that of the suture needle such that when pressure is exerted on the suture needle, it passes through the cornea button within a pre-designed depth range, and then exits through the surrounding corneal tissue, without further guidance from the surgeon.

Figure 5:
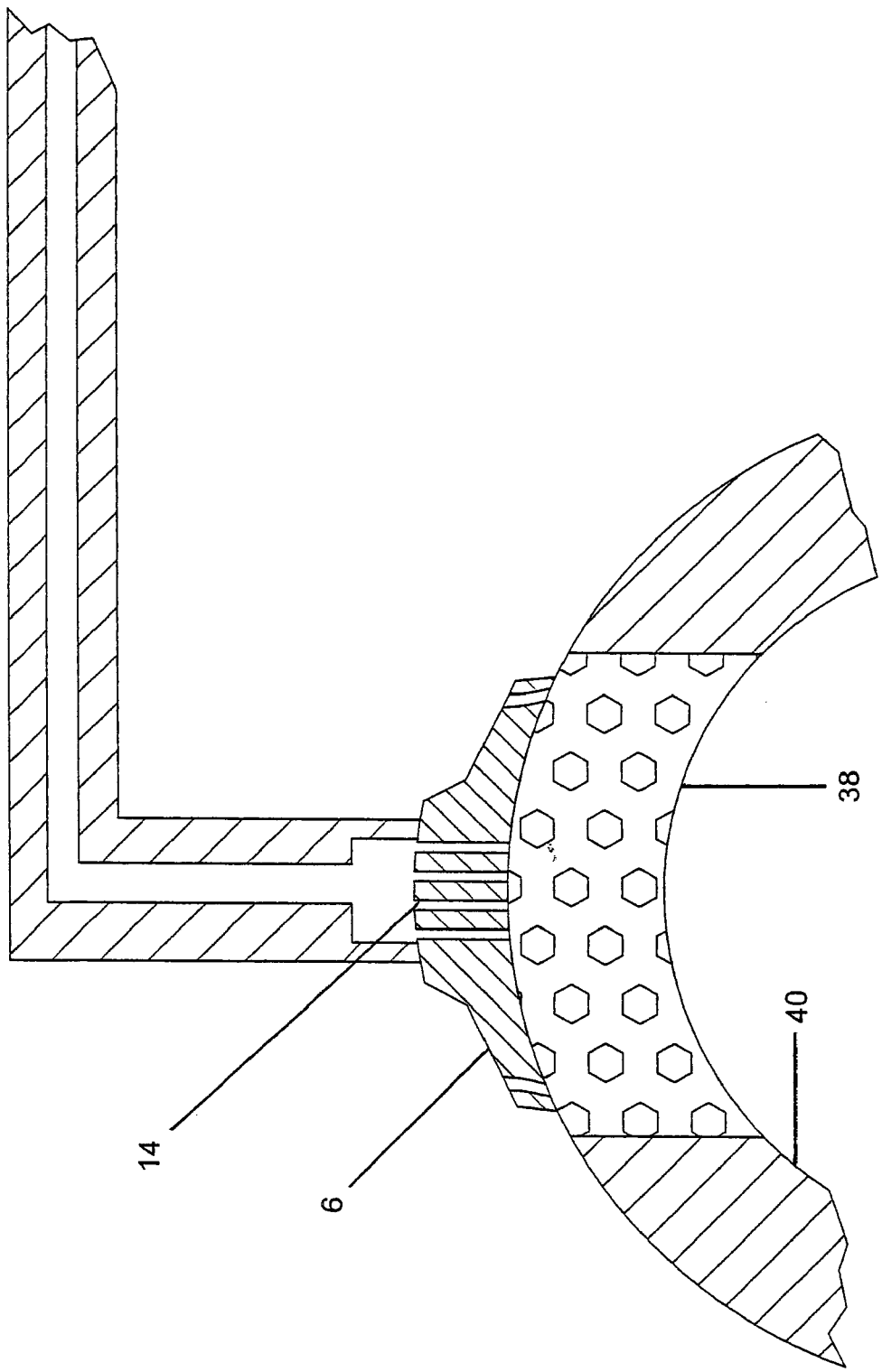
FIG. 5 illustrates a side sectional view of one embodiment of the removable base plate holding a cornea button.

FIG. 5 illustrates a side sectional view of one embodiment of removable base plate 6 holding cornea button 38. Negative pressure is exerted through suction ports 14 to hold cornea button 38 against removable base plate 6 as cornea button 38 is placed on the recipient's eye. The diameter of cornea button 38 is slightly larger than that of the corneal tissue removed from the recipient's eye, so that cornea button 38 fits snugly in the surrounding corneal tissue 40 in the recipient's eye. In this embodiment, the outer edge of cornea button 38 slightly exceeds that of removable base plate 6, allowing the surgeon to observe the edge of cornea button 38 and surrounding corneal tissue 40 as cornea button 38 is sutured onto the recipient's eye. Without wishing to be bound by this theory, it is believed that a larger donor button (e.g., 0.25–0.50 mm larger than the diseased trephined cornea) will help prevent post-op flattening. In an alternative embodiment, the outer edge of removable base plate 6 slightly exceeds that of cornea button 38, allowing the surgeon to rest the distal end of removable base plate 6 onto surrounding corneal tissue 40 as cornea button 38 is sutured onto the recipient's eye.

Figure 6:
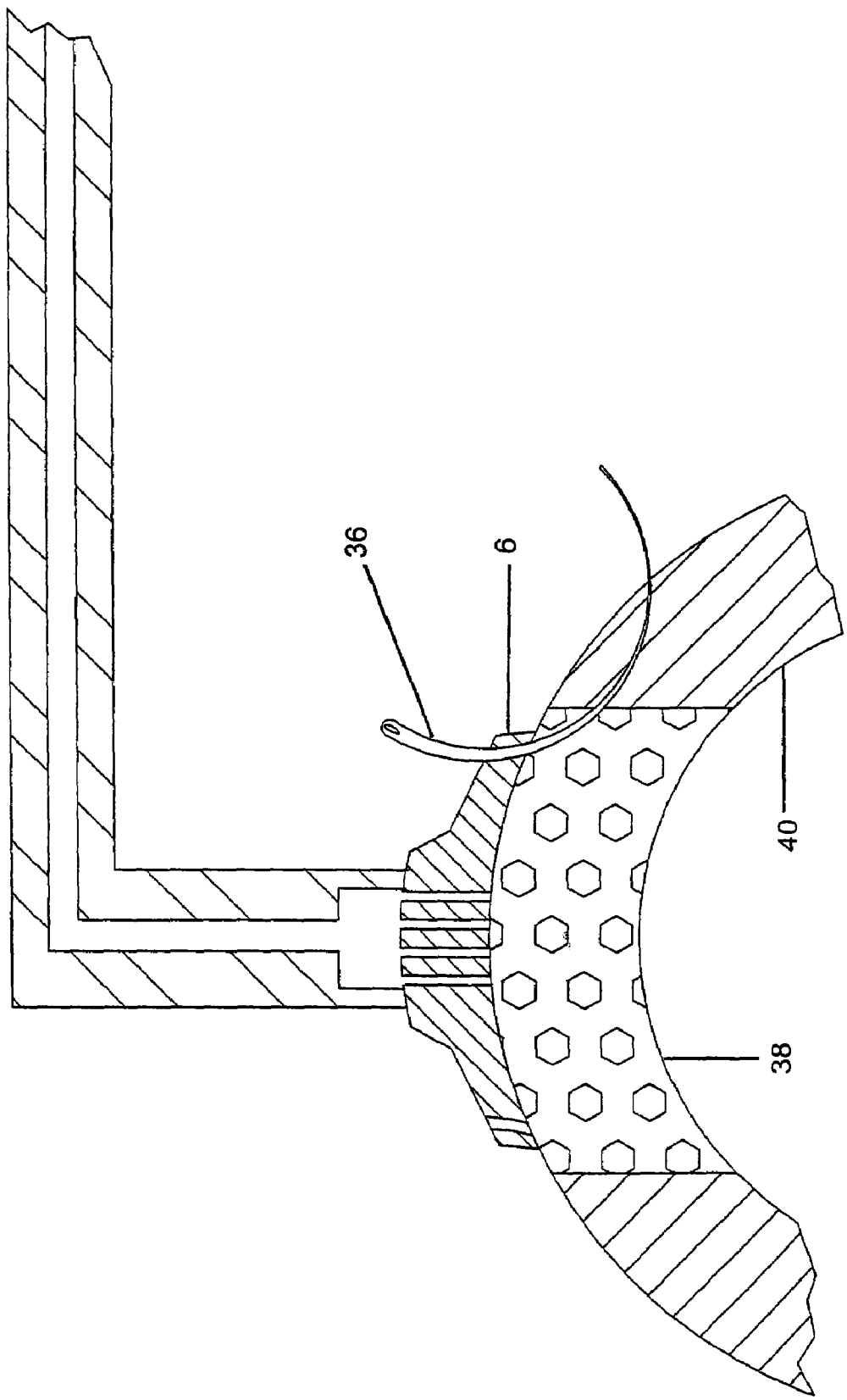
FIG. 6 illustrates a view of a suture needle as it passes through the cornea button and surrounding corneal tissue.

FIG. 6 illustrates a view of a suture needle 36 as it passes through cornea button 38 and surrounding corneal tissue 40. As pressure is exerted on suture needle 36, the contact surface of suture groove 16 guides the suture needle 36 into cornea button 38 and through the surrounding corneal tissue 40. The suture needle 36 fits snugly against the contact surface of suture groove16 to facilitate accurate and symmetrical placement of suture. The length of suture needle 36 is adapted to provide a sufficient area to grasp as suture needle 36 is passed through cornea button 38 and surrounding cornea tissue 40. In a preferred embodiment, to avoid damaging the needle point and swage area, the length of suture needle 36 is adapted to provide a constant grasping area of at least one-third the distance from the swaged end to the point.

A preferred method of transplanting a cornea, using cornea transplanter 2, is to remove healthy donor corneal tissue 34. A trephine device having a circular blade is used to remove the defective cornea from the recipient's eye. Donor corneal tissue 34 is then centrally placed on removable base plate 6 in support block 4, with the endothelial portion of donor corneal tissue 34 facing upwards. Donor corneal tissue 34 is then moistened using a preservative solution, such as VISCOAT® and HEALON® intraocular viscoelastic solutions. Negative pressure is then applied to the anterior surface of donor corneal tissue 34 to hold it in place. Lid 26 is then placed over support block 4 with cutting blade 24 facing towards support block 4, and inserts 28 and ports 30 are properly aligned. Once lid 26 and support block 4 are aligned, lid 26 is pressed onto support block 4 to cut a cornea button 38 having a slightly larger diameter (between approximately 0.25–0.50 mm) than the removed cornea portion. Lid 26 is then removed from support block 4 and cornea button 38 is visually inspected to ensure that it was properly cut. Support block filler 12 is then removed from support block 4 to provide access to removable base plate 6. Without releasing the negative pressure on cornea button 38, removable base plate 6 is then removed from support block 4, and positioned near the recipient's eye. Cornea button 38 is then placed onto the recipient's eye to fill the void created where the defective cornea portion was removed. Once cornea button 38 is properly positioned, suture needle 36 is inserted into a suture groove 16 using a needle holder, and then passed into cornea button 38 and through surrounding corneal tissue 40. The suture is then passed through suture groove slit 16, and the process is repeated until individual sutures have been passed through all of the suture grooves 16. The sutures are tied either before or after releasing the negative pressure. As necessary, the sutures may be adjusted, retied, or removed. Optionally, a running suture, one suture that connects all the suture grooves 16 together in a circular array, may be used. The running suture may also be combined with interrupted sutures or double running sutures.

The complete disclosures of all references cited in this specification are hereby incorporated by reference. In the event of an otherwise irreconcilable conflict, however, the present specification shall control.

I claim:

1. A device for transplanting donor corneal tissue onto a mammalian recipient's eye, comprising:
   (a) a cutting blade; wherein the dimensions and shape of said cutting blade are adapted to allow said cutting blade to cut a cornea button suitable for transplantation from the donor corneal tissue;
   (b) a removable, concave base plate comprising a proximal end having a plurality of suction ports, and a distal end having a plurality of suture grooves; wherein said suction ports are adapted to receive and distribute a negative pressure to hold the donor corneal tissue; and wherein said suture grooves have a size and shape adapted to guide a suture needle into the cornea button and through surrounding corneal tissue when the cornea button is placed on the recipient's eye;
   (c) a concave support block having a bore adapted to receive said base plate; wherein said block is adapted, so that when said base plate is positioned in said bore, said support block and said base plate form a smooth and continuous concave surface that approximates the curvature of the anterior surface of the corneal tissue; and
   (d) a vacuum device adapted to supply a negative pressure to the cornea button to hold the cornea button on said base plate;

wherein:
   (e) when negative pressure is applied to the donor corneal tissue, a cornea button may be cut from the donor corneal tissue, placed onto to the recipient's eye, and sutured to the remaining corneal tissue of the recipient.

2. A device as recited in claim 1, additionally comprising a handle attached to said base plate.

3. A device as recited in claim 2, wherein said handle is a syringe-type suction device.

4. A device as recited in claim 1, wherein the size of said cutting blade is adapted to cut the donor corneal tissue to a size that is slightly larger than said base plate.

5. A device as recited in claim 1, wherein the size of said cutting blade is adapted to cut the donor corneal tissue to a size that is slightly smaller than said base plate.

6. A device as recited in claim 1, additionally comprising a lid to hold said cutting blade, wherein said lid further comprises a plurality of inserts positioned at each corner; and wherein said support block further comprises ports located at the periphery of said support block; wherein said ports are adapted to receive said inserts to align the position of said lid in said support block.

7. A device as recited in claim 1, wherein said suture grooves are adapted to allow a suture needle to pass through the distal end of said removable, concave base plate as the suture needle is passed through the cornea button and surrounding recipient corneal tissue.

8. A method for surgically promoting grafting between a healthy donor cornea button and a mammalian recipient's remaining corneal tissue using a device as recited in claim 1; said method comprising holding the donor corneal tissue to the removable, concave base plate with negative pressure from the vacuum device; cutting a cornea button from the donor corneal tissue; placing the cornea button onto the recipient's eye, while maintaining negative pressure; and suturing the cornea button to the recipient's corneal tissue by suturing through the suture grooves.

9. A method as recited in claim 8, wherein the diameter of the cornea button is slightly larger than the portion of the cornea removed from the recipient.

10. A method as recited in claim 8, additionally comprising the steps of detaching the base plate from the support block, and positioning the base plate near the recipient's eye, while maintaining negative pressure on the cornea button, so that the cornea button fills the void created where a portion of the cornea was removed from the recipient's eye.

11. A method as recited in claim 8, additionally comprising the steps of inserting a suture needle into a suture groove, and passing the suture needle and suture into the cornea button and through the surrounding corneal tissue.

12. A method as recited in claim 11, wherein the suture is a running suture.

13. A method as recited in claim 11, additionally comprising the steps of passing the suture through the suture groove slit, and repeating the steps of claim 11 until sutures have been passed through all of the suture grooves.

* * * * *